United States Patent
Gajula et al.

(10) Patent No.: US 11,104,623 B2
(45) Date of Patent: Aug. 31, 2021

(54) PROCESS FOR ACTIVATING AN AROMATIZATION CATALYST

(71) Applicant: SABIC GLOBAL TECHNOLOGIES B.V., Bergen op Zoom (NL)

(72) Inventors: Sreenivasa Rao Gajula, Bangalore (IN); Amit Kumar, Bangalore (IN); Ziyad Kottavarithottil, Bangalore (IN); Suman Kumar Jana, Bangalore (IN); Eswara Rao Mupparaju, Bangalore (IN); Vinita Dubey, Bangalore (IN); Sivakumar Sreeramagiri, Bangalore (IN)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 0 days.

(21) Appl. No.: 16/976,340

(22) PCT Filed: Apr. 29, 2019

(86) PCT No.: PCT/IB2019/053502
§ 371 (c)(1),
(2) Date: Aug. 27, 2020

(87) PCT Pub. No.: WO2019/211727
PCT Pub. Date: Nov. 7, 2019

(65) Prior Publication Data
US 2021/0040015 A1    Feb. 11, 2021

Related U.S. Application Data

(60) Provisional application No. 62/664,360, filed on Apr. 30, 2018.

(51) Int. Cl.
*C07C 2/76* (2006.01)
*B01J 23/28* (2006.01)
(Continued)

(52) U.S. Cl.
CPC ............... *C07C 2/76* (2013.01); *B01J 23/28* (2013.01); *B01J 29/48* (2013.01); *B01J 37/084* (2013.01);
(Continued)

(58) Field of Classification Search
CPC ... C07C 2/76; C07C 2523/28; C07C 2529/48; C07C 15/04; B01J 23/28; B01J 29/48; B01J 37/084
See application file for complete search history.

(56) References Cited

U.S. PATENT DOCUMENTS 6,093,671 A * 7/2000 Wu ..................... B01J 27/22
                                                    208/136
6,599,374 B1 * 7/2003 Hirsch ............... C21B 13/0086
                                                    148/209
(Continued)

FOREIGN PATENT DOCUMENTS

WO    2011143303 A2    11/2011
WO    2019211727 A1    11/2019

OTHER PUBLICATIONS

International Search Report for International Application No. PCT/IB2019/053502; Application Filing Date: Apr. 29, 2019; dated Jul. 26, 2019, 6 pages.
(Continued)

*Primary Examiner* — Ali Z Fadhel
(74) *Attorney, Agent, or Firm* — Cantor Colburn LLP

(57) ABSTRACT

A process for activating an aromatization catalyst includes contacting an aromatization catalyst with a carburizing gas in a carburization reactor at a carburization pressure in a range of greater than 300 kPa to 800 kPa, or 500 kPa to 600 kPa, to obtain a calcined aromatization catalyst. The carburizing gas provides a carbon source, preferably the car-
(Continued)

burizing gas comprises at least one of methane, ethane, propane, butane, or carbon monoxide.

20 Claims, 6 Drawing Sheets

(51) Int. Cl.
  *B01J 29/48* (2006.01)
  *B01J 37/08* (2006.01)
(52) U.S. Cl.
  CPC ...... *C07C 2523/28* (2013.01); *C07C 2529/48* (2013.01)

(56) References Cited

U.S. PATENT DOCUMENTS

| | | | |
|---|---|---|---|
| 7,728,186 | B2 | 6/2010 | Iaccino et al. |
| 7,893,308 | B2 | 2/2011 | Sangar et al. |
| 8,735,310 | B2 | 5/2014 | Ma et al. |
| 9,266,100 | B2 | 2/2016 | Jana |
| 2002/0179186 | A1* | 12/2002 | Ebihara ............. C23C 8/20 148/216 |
| 2002/0179187 | A1* | 12/2002 | Ebihara ............. C23C 8/20 148/216 |
| 2007/0249740 | A1* | 10/2007 | Iaccino ............. C07C 15/04 518/726 |
| 2012/0036889 | A1* | 2/2012 | Iaccino ............. C10L 3/08 62/618 |
| 2013/0066126 | A1* | 3/2013 | Jana ............. B01J 29/068 585/420 |
| 2016/0121311 | A1* | 5/2016 | Davidian ............. C07C 1/0445 518/717 |

OTHER PUBLICATIONS

Rahman, et al., "Impact of the presence of Mo carbide species prepared ex situ in Mo/HZSM-5 on the catalytic properties in methane aromatiziation", Applied Catalysis A, General 558 (2018) 67-90.

Tempelman, et al., "Activation of Mo/HZSM-5 for methane aromatization", Chinese Journal of Catalysis 36 (2015) 829-837.

Written Opinion for International Application No. PCT/IB2019/053502; Application Filing Date: Apr. 29, 2019; dated Jul. 26, 2019, 10 pages.

* cited by examiner

PROCESS FOR ACTIVATING AN AROMATIZATION CATALYST

CROSS REFERENCE TO RELATED APPLICATIONS

This application is a National Stage application, i.e., a 371 of PCT/IB2019/053502, filed Apr. 29, 2019, which claims the benefit of U.S. Provisional Application No. 62/664,360, filed Apr. 30, 2018, both of which are incorporated herein by reference in their entirety.

BACKGROUND

Methane aromatization is a promising route for production of benzene. In the aromatization reaction, aromatization catalysts can be used to convert the methane to benzene. Aromatization catalysts (e.g., molybdenum) can be carburized, for example, at atmospheric pressure, to form carbides (e.g., molybdenum carbide) that are active species in the aromatization catalyst (i.e., the aromatization catalyst is activated).

However, in order for conversion of methane to benzene by aromatization to be economically viable in terms of capital expenditures, an increased benzene productivity in an amount of, for example, greater than 300 grams of benzene produced per kilogram of catalyst per hour (g benzene/kgCat./hr), or desirably greater than or equal to 600 g benzene/kgCat./hr, can be required. Such levels of benzene productivity may not be obtainable with current processes.

Additionally, as the aromatization reaction progresses, the catalyst activity and associated benzene productivity can decrease due to formation of coke on the aromatization catalyst (i.e., coking). This coking can decrease the life of the aromatization catalyst. Such a decrease in the benzene productivity and life of the aromatization catalyst can affect the technological and economic viability of methane aromatization as a route for production of benzene.

U.S. Pat. No. 9,266,100 relates to a method for producing a zeolite catalyst for aromatization of a lower alkane, a zeolite catalyst for aromatization of a lower alkane obtainable by the method and a process for aromatization of a lower alkane using the zeolite catalyst.

Therefore, it would be desirable to provide improved methods for producing aromatization catalysts for the production of benzene to enable viable commercialization.

BRIEF DESCRIPTION OF DRAWINGS

The following figures are exemplary embodiments wherein the like elements are numbered alike and which are presented for the purposes of illustrating the exemplary embodiments disclosed herein and not for the purposes of limiting the same.

Figure 1:
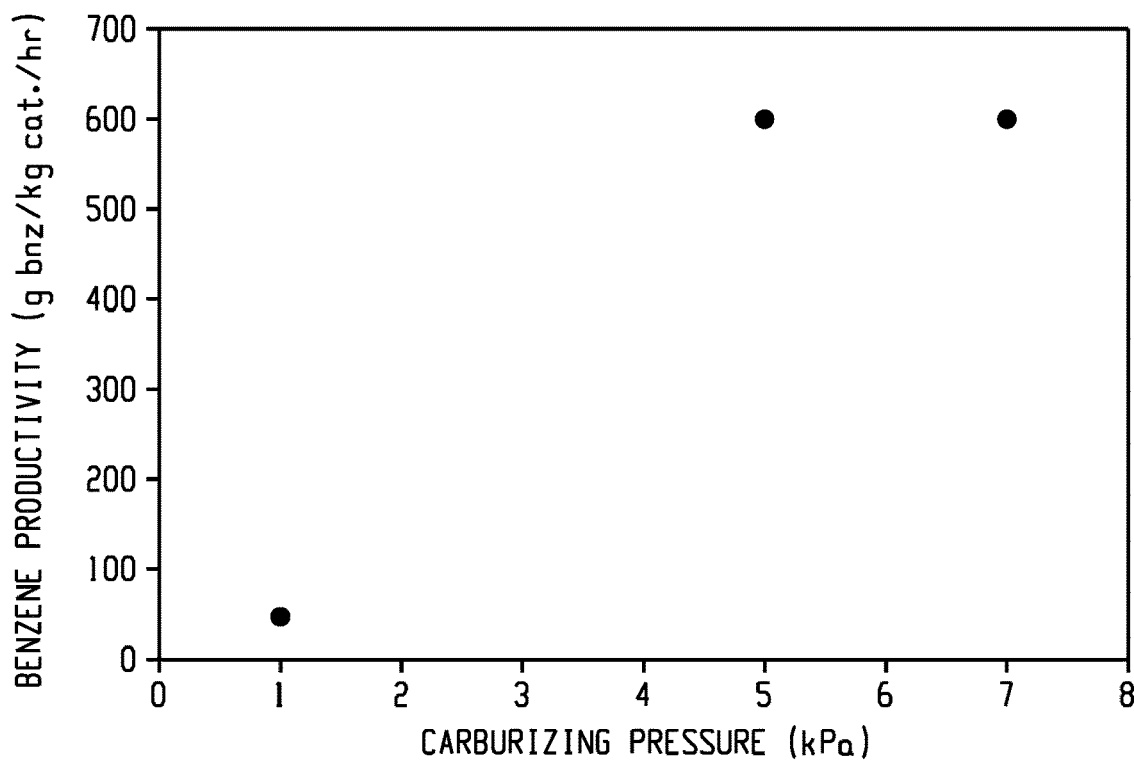
FIG. 1 is a graphical illustration of benzene productivity with carburization pressure for Example 1.

The above described and other features are exemplified by the following detailed description, examples, and claims.

DETAILED DESCRIPTION

Disclosed herein are processes for activating (i.e., carburizing) aromatization catalysts for use in aromatization of methane to obtain an aromatization product comprising at least one of benzene, naphthalene, toluene, xylene, ethylbenzene, or methyl-naphthalene (i.e., aromatic products), and preferably for use in aromatization of methane to obtain benzene. Desirably, use of the processes described herein to activate (i.e., carburize) aromatization catalysts result in a greater benzene productivity during aromatization of methane and a greater stability of the aromatization catalyst as compared to aromatization catalysts produced by previous processes that do not include the methods for carburizing the aromatization catalyst as described herein. Previous processes for producing aromatization catalysts suffered from difficulties in achieving and maintaining high productivity of benzene during aromatization of methane.

Desirably, the present processes for carburizing an aromatization catalyst can include contacting the aromatization catalyst with a carburizing gas in a system, e.g., carburization reactor, increasing an absolute pressure of the system to a carburization pressure in a range of greater than 300 kilopascals (kPa) to 800 kPa (such as 325 kPa to 800 kPa), for example, in a range of 400 kPa to 700 kPa, e.g., 500 kPa to 600 kPa or 450 kPa to 550 kPa. The system can be maintained at the carburization pressure for a time period equal to or greater than 10 minutes, preferably 60 minutes to 540 minutes, e.g., 240 minutes to 480 minutes. Surprisingly, it was determined that a pressurized carburization of the aromatization catalyst resulted in greater benzene productivity throughout the aromatization reaction as compared to previous activation processes carried out at atmospheric pressure. For instance, the benzene productivity can be equal to or greater than 300 grams of benzene per kilogram of catalyst per hour (g benzene/kgCat./hr), for example, equal to or greater than 400 g benzene/kgCat./hr, in a range of 500 g benzene/kgCat./hr to 800 g benzene/kgCat./hr, preferably in a range of 600 g benzene/kgCat./hr to 700 g benzene/kgCat./hr.

Without wishing to be bound by theory, it is believed that carburizing the aromatization catalyst to form carbides under high pressure results in less mobile phases of the activated catalyst on an inorganic support. The lesser amount of mobile phases of the activated catalyst results in greater stability in catalyst activity, which translates to greater benzene productivity. Thus, decreases in benzene productivity due to coking can be reduced or offset by the present processes.

The process for carburizing the aromatization catalyst can include increasing a temperature in the carburization reactor from room temperature to a temperature in a range of 300° C. to 900° C., or 350° C. to 800° C., preferably 400° C. to 700° C. The carburization reactor can be maintained at a carburization temperature for a time period equal to or greater than 10 minutes, preferably 60 minutes to 540 minutes, e.g., 240 minutes to 480 minutes. A temperature in the carburization reactor can be increased at a rate in a range of 2° C. to 10° C. per minute.

The carburizing gas can be contacted with the aromatization catalyst at a gas hourly space velocity (GHSV) in a range of 1,000 milliliters per gram of catalyst per hour (ml·g$^{-1}$ hr$^{-1}$) to 12,000 ml·g$^{-1}$ hr$^{-1}$, or 5,000 ml·g$^{-1}$ hr$^{-1}$ to 11,000 ml·g$^{-1}$ hr$^{-1}$, preferably 7,000 ml·g$^{-1}$ hr$^{-1}$ to 10,000 ml·g$^{-1}$ hr$^{-1}$.

Any gas providing a carbon source can be included in the carburizing gas. The carburizing gas can include at least one of methane, ethane, propane, butane, or carbon monoxide along with hydrogen. Preferably, the carburizing gas includes methane; e.g., methane and hydrogen. A volume ratio of the carbon source (e.g., of the methane) to diluent (e.g., the hydrogen) can be in a range of 5:95 to 30:70, or 10:90 to 25:75, preferably 15:85 to 25:75; e.g., 20:80.

Desirably, the aromatization catalyst includes a catalytic metal on an inorganic support. The inorganic support can be an inorganic oxide such as zeolite, preferably a zeolite in the hydrogen form. The zeolite can be at least one of a zeolite Y, zeolite X, mordenite, ZSM-5 (such as HZSM-5), ALPO-5, VPI-5, FSM-16, MCM-22, or MCM-41. The zeolite may be MCM-22. Desirably, the zeolite comprises HZSM-5. The zeolite can have a silica to alumina molar ratio in a range of 10:1 to 50:1, or 13:1 to 30:1, preferably 25:1 to 30:1.

The aromatization catalyst can include the catalytic metal in an amount in a range of 2 weight percent (wt. %) to 7 wt. %, or 3 wt. % to 6 wt. %, based on the weight of the inorganic support. The catalytic metal can include at least one of chromium, cobalt, gallium, iron, magnesium, molybdenum, vanadium, or zinc, preferably the catalyst comprises molybdenum.

The aromatization catalyst can be at least one of dried or calcined before carburizing the aromatization catalyst.

The aromatization catalyst can be dried at a temperature of 120° C. in an air oven for a time in a range of 10 hours to 20 hours. The aromatization catalyst can then be calcined by heating the aromatization catalyst starting from room temperature at a range of 500° C. to 600° C. for a time in a range of 10 hours to 20 hours at a rate of 2° C. to 10° C. per minute in a calcination furnace using flowing air (e.g., of 5% to 30% relative humidity, 0.1 to 1 milliliters per second (ml/s) velocity). After calcination the aromatization catalyst can be cooled to room temperature in flowing air (e.g., of 5% to 30% relative humidity, 0.1 to 1 ml/s velocity).

After calcination and before carburization, the aromatization catalyst can be cooled to a temperature less than the calcining temperature.

The aromatization catalyst can be in the form of an extrudate, which allows the aromatization catalyst to be handled more easily (e.g., without powder handling considerations such as caking of the powder, loss of powder to the environment, lack of precision in dosing, etc.) and also allows tuning of the reactor conditions (e.g., methane flow characteristics) based on the shape and size of the extrudates. For instance, the aromatization catalyst can be combined with at least one of silica containing source, hydroxyl propyl methyl cellulose, or water, and extruded to form extrudates. The extrudates can be cylindrical, spherical, irregular-shaped, or any other shape used in an aromatization reaction. The extrudates can have a dimension with a size ranging from 1 millimeter (mm) to 100 millimeters, or 5 millimeters to 50 millimeters, preferably 10 millimeters to 25 millimeters.

A calcined aromatization catalyst can be activated (i.e., carburized) by the above-described process.

A process for aromatization of methane can include reacting the methane in the presence of the above-described calcined aromatization catalyst to obtain at least one of benzene, naphthalene, toluene, xylene, ethylbenzene, or methyl-naphthalene, preferably benzene.

The process of aromatization of methane can include feeding at least one of carbon dioxide or carbon monoxide to an aromatization reactor in which methane is reacted in the presence of the calcined aromatization catalyst. The combined amount of carbon dioxide and carbon monoxide can be in a range of 0.6 volume percent (vol. %) to 1 vol. %, or 0.6 vol. % to 0.8 vol. %, or 0.7 vol. % to 0.8 vol. %, based on the total volume of the methane, carbon dioxide, and carbon monoxide. Without wishing to be bound by theory, it is believed that carbon dioxide, carbon monoxide, or both react with coke precursors to subdue or prevent coke formation on the aromatization catalyst. Thus, decreases in the aromatization catalyst activity and benzene productivity over time during the aromatization reaction can be reduced.

The methane can react to form benzene at a temperature in a range of 700° C. to 850° C., or 700° C. to 825° C., preferably 700° C. to 800° C.

The methane can react at a pressure in a range of 100 kPa to 1,000 kPa, or 200 kPa to 900 kPa, preferably 300 kPa to 800 kPa. For example, the methane can be at a pressure of greater than 400 kPa, or in a range of 400 kPa to 800 kPa, or 450 kPa to 750 kPa, or 500 kPa to 700 kPa, or 500 kPa to 600 kPa.

The methane can be fed to the aromatization reactor at a gas hourly space velocity in a range of 1,000 ml·g$^{-1}$ hr$^{-1}$ to 30,000 ml·g$^{-1}$ hr$^{-1}$, or 2,000 ml·g$^{-1}$ hr$^{-1}$ to 29,000 ml·g$^{-1}$ hr$^{-1}$, preferably 3,000 ml·g$^{-1}$ hr$^{-1}$ to 28,000 ml·g$^{-1}$ hr$^{-1}$.

A conversion of the methane can be equal to or greater than 5%, or greater than 10%, preferably greater than 15%. As used herein, "conversion" refers to the moles of methane converted to benzene, naphthalene, toluene, xylene, ethylbenzene, methyl-naphthalene, and by-products divided by the moles of methane fed to the aromatization reactor.

The benzene productivity can be greater than or equal to 300 g benzene/kgCat./hr, for example, greater than or equal to 400 g benzene/kgCat./hr, in a range of 500 g benzene/kgCat./hr to 800 g benzene/kgCat./hr, preferably 600 g benzene/kgCat./hr to 700 g benzene/kgCat./hr.

At least one of benzene, naphthalene, toluene, xylene, ethylbenzene, or methyl-naphthalene can be produced by the above-described process for aromatization of methane.

This disclosure is further illustrated by the following examples, which are non-limiting.

EXAMPLES

Aromatization Catalyst Preparation

The following procedure was used to prepare the aromatization catalysts and extrudates used in the following Examples.

A HZSM-5 zeolite catalyst support was calcined in a furnace under flowing air (25° C., 15% relative humidity, 0.5 milliliters/second velocity) and increasing the temperature 2.5° C. per minute until a temperature of 540° C. was reached and kept at the same temperature for 16 hours. The total calcination time was approximately 20 hours.

Ammonium hepta molybdate salt (13.81 grams) was dissolved in 280 milliliters (ml) of demineralized water at 25° C. to produce an ammonium hepta molybdate solution. The pH of the ammonium hepta molybdate solution was 5.98. The pH of the ammonium hepta molybdate solution (5 wt. % concentration) was adjusted with a dropwise addition of an aqueous ammonia solution (25 wt. % concentration) until a pH of 9.8 was reached. Then, the HZSM-5 zeolite catalyst support was contacted with the ammonium hepta molybdate solution for 2 hours to allow the molybdenum to penetrate the pores and react with the active sites of the HZSM-5 zeolite at 25° C. in a 500 milliliter three-neck round-bottom flask while the ammonium hepta molybdate solution was stirred at 300 rotations per minute. The aqueous ammonia was added during the stirring until a pH of 9.79 was reached and a catalyst slurry was obtained. Next, the flask was placed in a water bath at a temperature of 95° C. and continuously stirred until the water from the catalyst slurry was removed.

The aromatization catalyst was removed from the flask, crushed into a powder, and dried at a temperature of 120° C. in an air oven for 12 hours.

Calcination was carried out by heating the aromatization catalyst starting from room temperature to 550° C. at a rate of 2.5° C. per minute in a calcination furnace in flowing air (25° C., 15% relative humidity, 0.5 ml/s velocity) and calcined at 550° C. for 16 hours. After calcination, the aromatization catalyst was cooled to room temperature in flowing air (25° C., 15% relative humidity, 0.5 ml/s velocity).

The aromatization catalyst was used to prepare extrudates with a composition of 74 wt. % aromatization catalyst and 26 wt. % silica, based on the total weight of aromatization catalyst and silica. For a batch of 100 grams of extrudates, 69 grams of aromatization catalyst was mixed with 24 grams of silica (from 60 grams of a 40 wt. % colloidal silica suspension, Aldrich LUDOX™ AS-40 added dropwise during the mixing) and 7.04 grams of hydroxyl propyl methyl cellulose. The mixture was ground for 15 minutes in a mortar and pestle. Deionized water was added dropwise in an amount of 20 wt. % based on the total weight of the mixture, to produce a dough for extrusion. The resulting mixture was extruded in a twin screw extruder to produce cylindrical extrudates (1.5 millimeter (mm) diameter and 15 mm length). The extrudates were dried overnight at 120° C. in an air oven. The extrudates were then calcined by heating from room temperature to 550° C. at a rate of 2.5° C. per minute in a calcination furnace in flowing air (25° C., 15% relative humidity, 0.5 milliliters/second velocity) for 16 hours. After calcination the extrudates were cooled to room temperature in flowing air (25° C., 15% relative humidity, 0.5 ml/s velocity).

Inductively coupled plasma mass spectroscopy was used to measure the molybdenum content in the extrudates before carburization. The molybdenum content was 3.8 wt. %, based on the total weight of the aromatization catalyst.

Next, 4 grams of the extrudates were loaded in a packed bed reactor made of stainless steel. Inert alpha alumina powder with sizes in a range of 250 micrometers to 500 micrometers was packed above and below the extrudates to provide support in the packed bed. A total of 2-4 grams of inert alpha alumina powder was loaded for each Example.

The extrudates were next subjected to carburization. Carburization was carried out with a carburizing gas including 20 vol. % methane and 80 vol. % hydrogen, based on total volume of the carburizing gas.

Carburization was carried out at varying pressures, as will be further detailed. While maintaining the specific pressure, unless specified otherwise, the carburization temperature was increased from room temperature to 650° C. at a heating rate of 2.5° C. per minute, and the temperature of 650° C. was maintained for 50 minutes.

Unless specified otherwise, methane was fed to the aromatization reactor to carry out the aromatization reaction at a gas hourly space velocity of 12,500 ml·g$^{-1}$ h$^{-1}$, at an absolute pressure of 500 kPa, and a temperature of 800° C.

Example 1

The effect of the carburization pressure on the benzene productivity was demonstrated by carburizing three aromatization catalysts at carburization pressures of 100 kPa, 500 kPa, and 700 kPa. The carburizing gas was fed to the carburization reactor at a GHSV of 7,500 ml·g$^{-1}$ h$^{-1}$. As shown in FIG. 1, the maximum benzene productivity increased when the carburization pressure was 500 kPa or 700 kPa, as compared to 100 kPa.

Example 2

Figure 2:
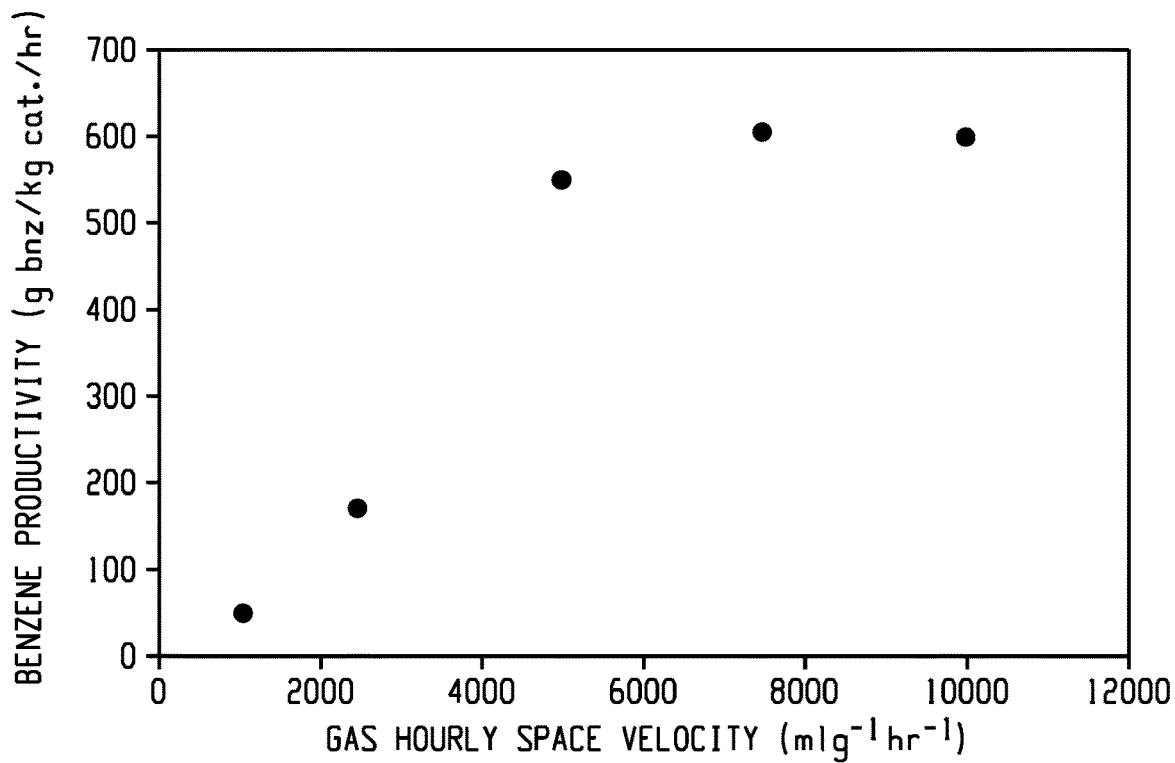
FIG. 2 is a graphical illustration of benzene productivity with gas hourly space velocity (GHSV) of the carburizing gas for Example 2.

The effect of the GHSV of the carburizing gas on the benzene productivity was demonstrated by carburizing five aromatization catalysts and feeding the carburizing gas at GHSVs of 1,000 ml·g$^{-1}$ h$^{-1}$, 2,250 ml·g$^{-1}$ h$^{-1}$, 5,000 ml·g$^{-1}$ h$^{-1}$, 7,500 ml·g$^{-1}$ h$^{-1}$, and 10,000 ml·g$^{-1}$ h$^{-1}$. The carburization pressure was 500 kPa. As seen in FIG. 2, the maximum benzene productivity during the reaction increased until a GHSV of 7,500 ml·g$^{-1}$ h$^{-1}$ was used. The benzene productivity remained the same as the GHSV was increased from 7,500 ml·g$^{-1}$ h$^{-1}$ to 10,000 ml g$^{-1}$ h$^{-1}$.

Examples 3-6

Figure 3:
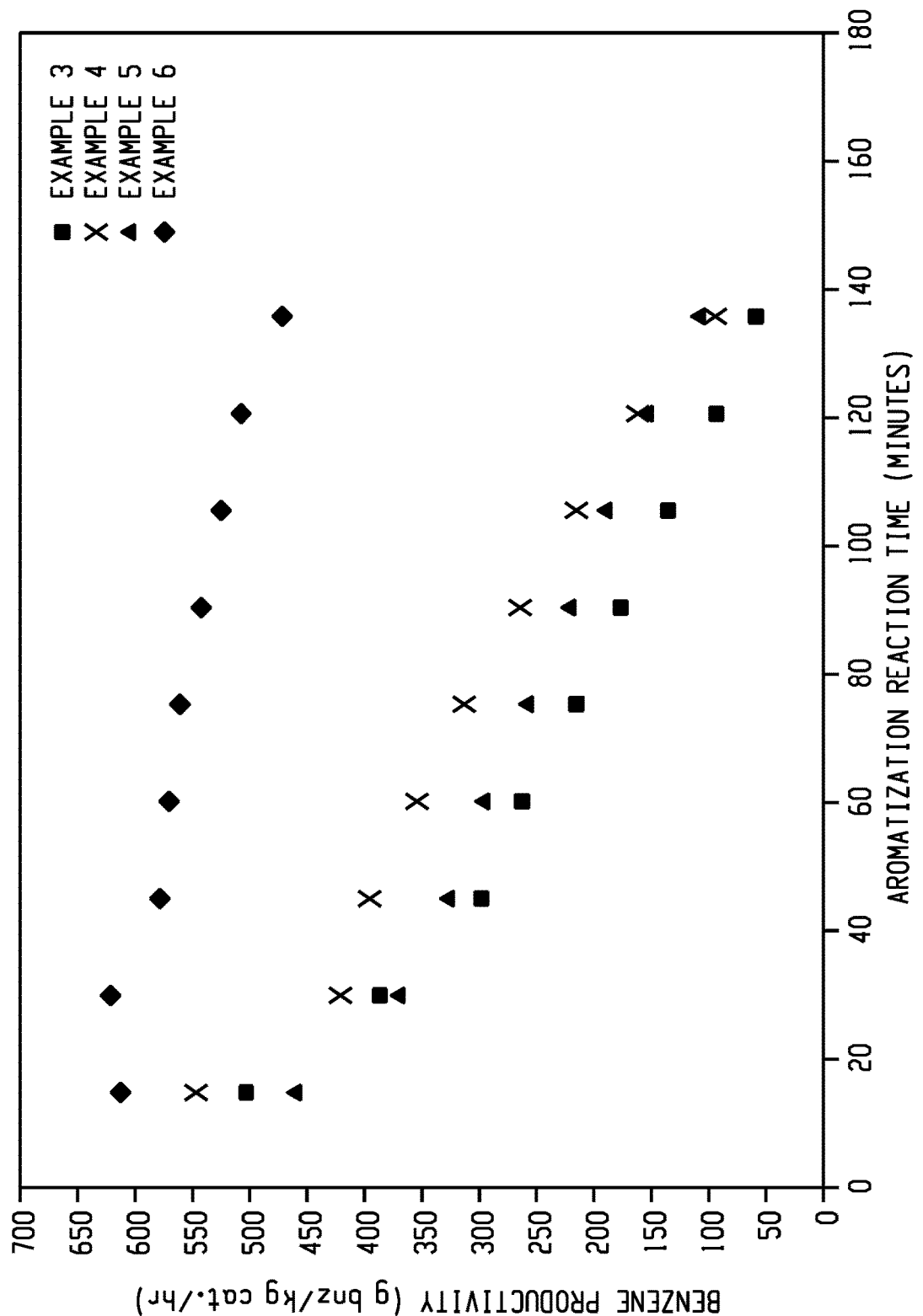
FIG. 3 is a graphical illustration of benzene productivity with aromatization reaction time for Examples 3-6.

The effect of the amount of carbon dioxide fed to the aromatization reactor on the benzene productivity was demonstrated by carrying out four aromatization reactions feeding carbon dioxide in amounts of 0.18 vol. %, 0.36 vol. %, 0.54 vol. %, and 0.72 vol. % (Examples 3, 4, 5, and Example 6, respectively), based on the total volume of the methane and carbon dioxide. Each of the aromatization catalysts was activated (i.e., carburized) at a carburization pressure of 500 kPa and the carburizing gas was fed to the carburization reactor at a GHSV of 7,500 ml·g$^{-1}$ h$^{-1}$. As seen in FIG. 3, the benzene productivity increased as the amount of carbon dioxide was increased. The amount of carbon dioxide can be up to 1 vol. %, based on the total volume of the methane and carbon dioxide.

Examples 7 and 8 and Comparative Example 9

The effect of greater carburization pressure and carbon dioxide in the aromatization reaction was demonstrated in Examples 7 and 8 and Comparative Example 9. In Examples 7 and 8, the extrudates were carburized at a carburization pressure of 500 kPa. In Comparative Example 9, the extrudates were carburized at a carburization pressure of 100 kPa. The carburizing gas was fed to the carburization reactor at a GHSV of 7,500 ml·g$^{-1}$ h$^{-1}$.

Aromatization of methane was carried out in Examples 7 and 9 without carbon dioxide. Aromatization of methane was carried out in Example 8 with 0.72 vol. % carbon dioxide, based on the total volume of the methane and the carbon dioxide.

Figure 4:
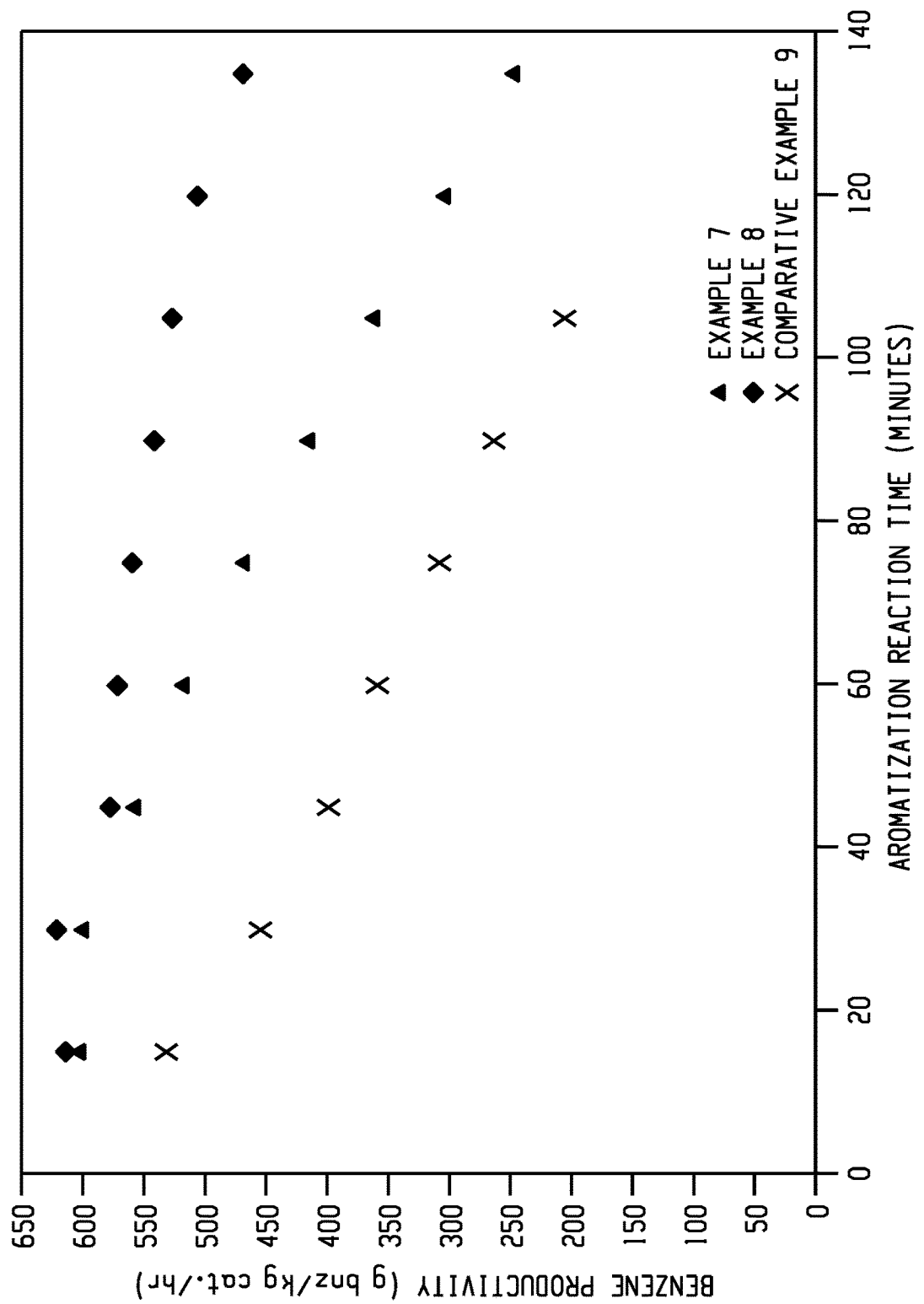
FIG. 4 is a graphical illustration of benzene productivity with aromatization reaction time for Examples 7 and 8 and Comparative Example 9.

As shown in FIG. 4, Example 7, in which the catalyst was carburized at a pressure of 500 kPa, demonstrated greater benzene productivity than Comparative Example 9, in which the catalyst was carburized at a pressure of 100 kPa. However, Example 8, in which carbon dioxide was included in the aromatization gas, maintained a higher benzene productivity than Example 7, in which carbon dioxide was not included in the aromatization gas fed to the aromatization reactor. Without wishing to be bound by any theories, it is believed that inclusion of carbon dioxide in the aromatization gas fed to the aromatization reactor decreased deposition of a by-product of the aromatization reaction, coke, on the active surface of the catalyst. Thus, deactivation of the catalyst, which reduces methane conversion, was reduced.

Examples 11 and 12 and Comparative Examples 13 and 14

The effect of the combination of greater carburization pressure was further demonstrated in Examples 11 and 12 and Comparative Examples 13 and 14. In Examples 11 and 12, catalysts were carburized at carburization pressures of 700 kPa and 500 kPa, respectively, and in Comparative Examples 13 and 14 catalysts were carburized at carburization pressures of 300 kPa and 100 kPa, respectively.

The carburizing gas, which included 80 vol. % $H_2$ and 20 vol. % methane was fed to the carburization reactor at a GHSV of 7,500 ml·$g^{-1}$ $h^{-1}$ and a temperature of 25° C., and the temperature was increased at a rate of 2.5° C. per minute to a temperature of 650° C., at which point the temperature was maintained for 50 minutes.

Thereafter, $H_2$ was fed to the carburization reactor at a rate of 400 milliliters per minute, at a temperature from 650° C. to 780° C., and at a reactor pressure of 300 kPa. Aromatization of methane was carried out with a GHSV of 3,000 ml·$g^{-1}$ $h^{-1}$ having an aromatization gas including 97 vol. % methane and 3 vol. % carbon dioxide, at a temperature of 780° C., and a pressure of 300 kPa.

Figure 5A:
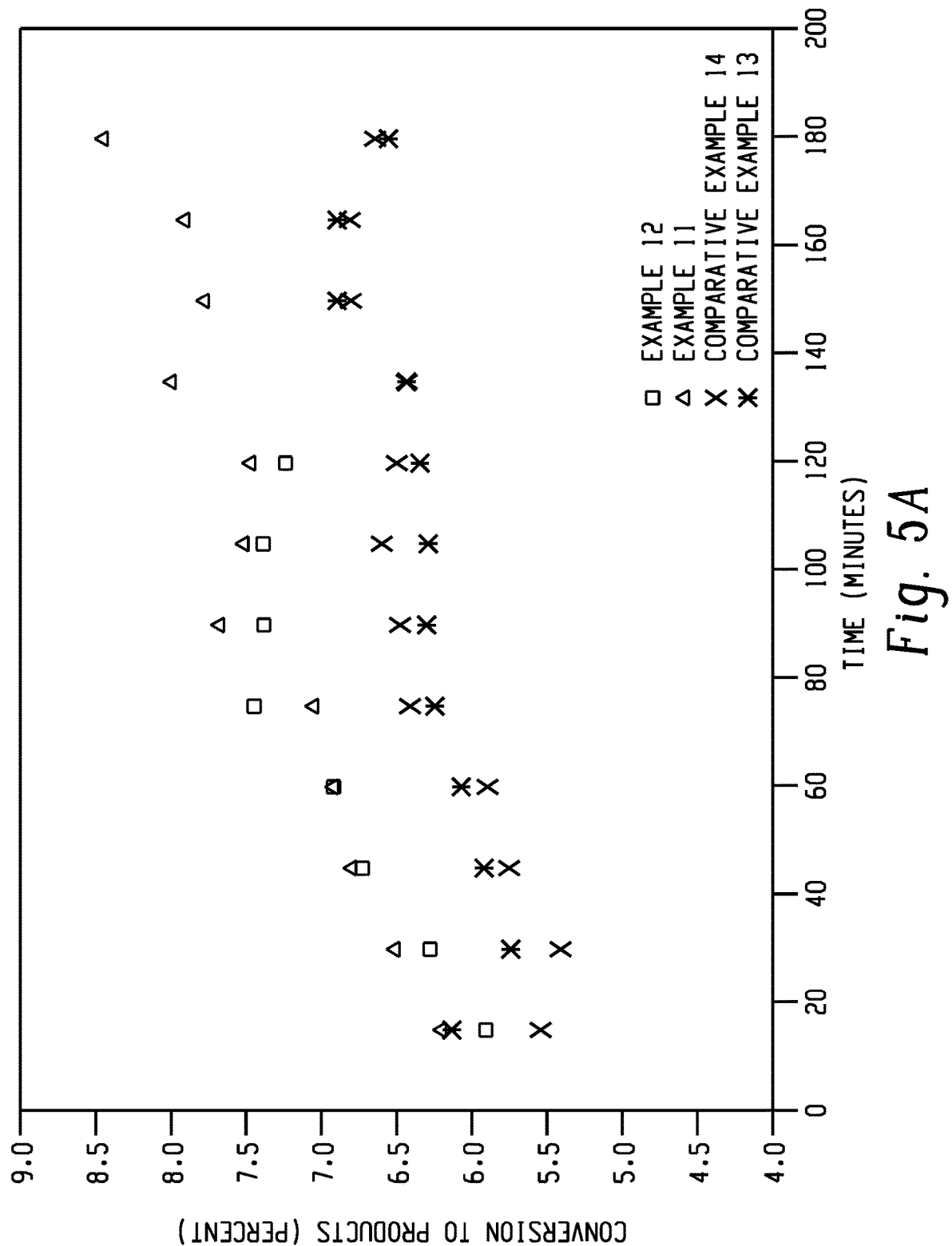
FIGS. 5A-5C are graphical illustrations of percent conversion to products, benzene productivity, and percent benzene yield, respectively, with aromatization reaction time for Examples 11 and 12 and Comparative Examples 13 and 14.
Figure 5B:
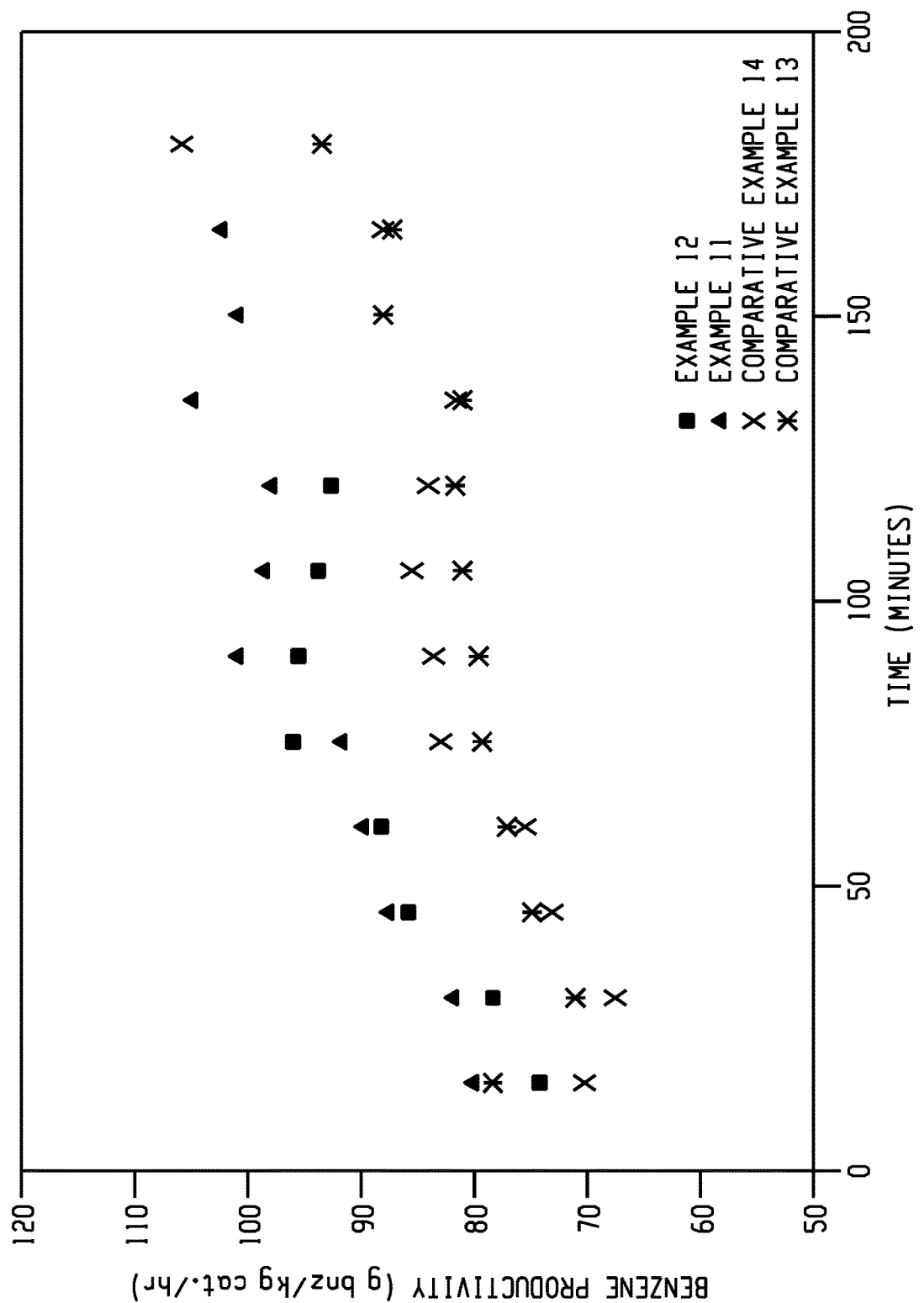
Figure 5C:
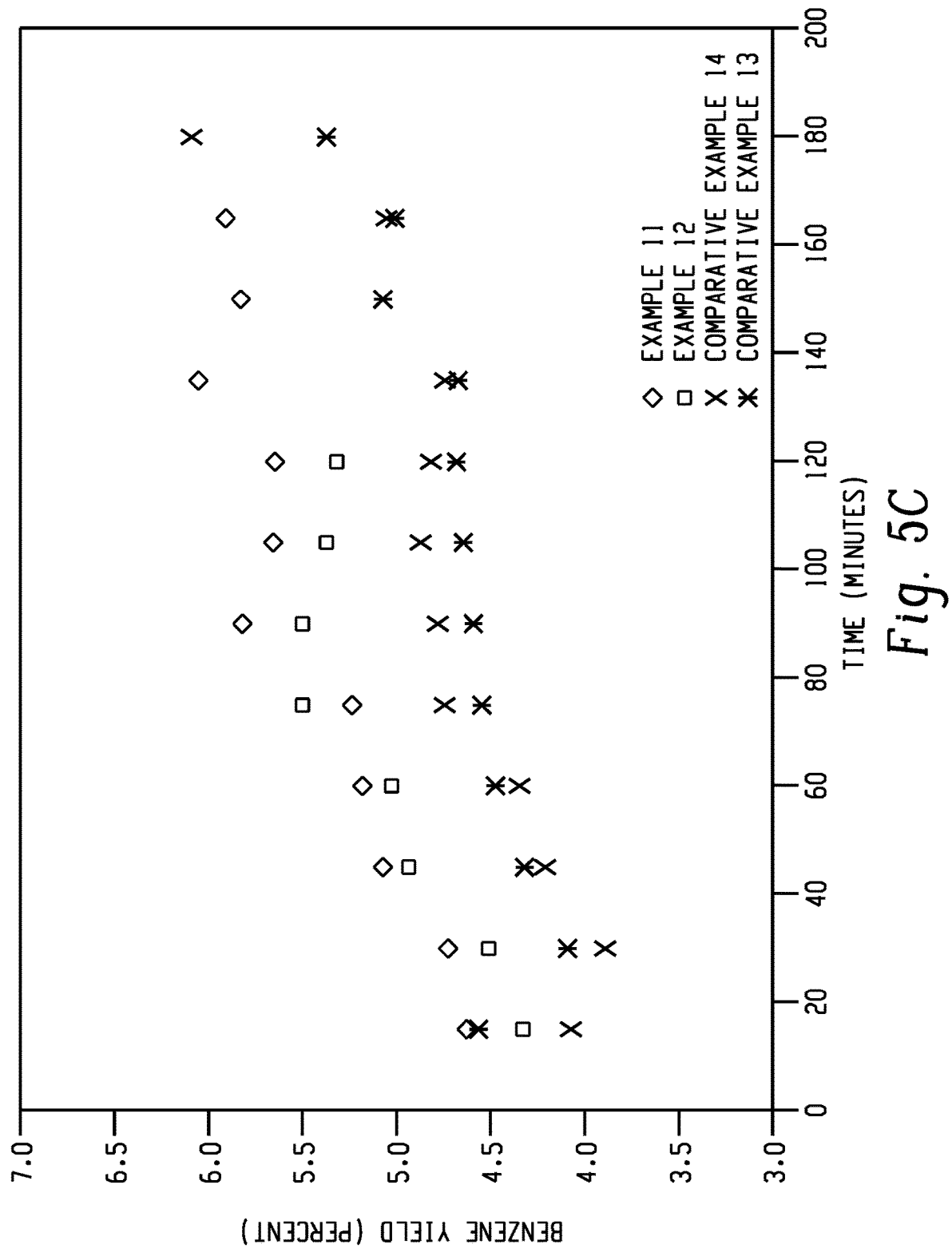

As shown in FIGS. 5A, 5B, and 5C, Examples 11 and 12 showed greater percent conversion to products, benzene productivity, and percent benzene yield than Comparative Examples 13 and 14. As the catalysts of Examples 11 and 12 were carburized at pressures of 700 kPa and 500 kPa, respectively, and the catalysts of Comparative Examples 13 and 14 were carburized at pressures of 300 kPa and 100 kPa, respectively, it can be seen that carburization at a pressure of greater than 300 kPa provide improvements in percent conversion to products, benzene productivity, and percent benzene yield in a subsequent aromatization reaction using the carburized catalyst.

Thus, the methods of the present disclosure for carburizing an aromatization catalyst provide increased methane conversion, increased yield of aromatic products, or preferably increased methane conversion and increased yield of aromatic products. Such improvements result from increased benzene productivity throughout an aromatization reaction, as compared to processes that activate the aromatization catalyst at pressures less than or equal 300 kPa, for example, less than or equal to 100 kPa. Greater benzene productivity is also indicative of increased catalyst stability. These improvements in methane conversion and/or yield of aromatic products under pressure conditions improves the commercial viability of methane aromatization processes.

Aspect 1: A process for activating an aromatization catalyst, the process comprising contacting an aromatization catalyst with a carburizing gas in a carburization reactor at a carburization pressure in a range of greater than 300 kPa to 800 kPa, or 500 kPa to 600 kPa, to obtain a calcined aromatization catalyst; wherein the carburizing gas provides a carbon source, preferably the carburizing gas comprises at least one of methane, ethane, propane, butane, or carbon monoxide.

Aspect 2: The process of Aspect 1, further comprising maintaining the carburization reactor at the carburization pressure for a time greater than 10 minutes, preferably 60 minutes to 540 minutes, or 240 minutes to 480 minutes.

Aspect 3: The process of Aspect 1 or Aspect 2, further comprising increasing a temperature in the carburization reactor from room temperature to a temperature in a range of 300° C. to 900° C., or 350° C. to 800° C., preferably 400° C. to 700° C., during contacting of the aromatization catalyst with the carburizing gas.

Aspect 4: The process of Aspect 3, wherein increasing the temperature in the carburization reactor comprises increasing the temperature at a rate in a range of 2° C. to 10° C. per minute.

Aspect 5: The process of any one or more of the preceding aspects, wherein the carburizing gas is fed to the carburization reactor at a gas hourly space velocity in a range of 1,000 ml·$g^{-1}$ $hr^{-1}$ to 12,000 ml·$g^{-1}$ $hr^{-1}$, or 5,000 ml $g^{-1}$ $hr^{-1}$ to 11,000 ml·$g^{-1}$ $hr^{-1}$, preferably 7,000 ml·$g^{-1}$ $hr^{-1}$ to 10,000 ml·$g^{-1}$ $hr^{-1}$.

Aspect 6: The process of any one or more of the preceding aspects, wherein the carburizing gas comprises hydrogen, methane, ethane, propane, butane, or carbon monoxide, preferably methane and hydrogen, and wherein a volume ratio of methane to hydrogen is in a range of 5:95 to 30:70, or 10:90 to 25:75, preferably 15:85 to 20:80.

Aspect 7: The process of any one or more of the preceding claims, wherein the aromatization catalyst comprises a catalytic metal on an inorganic support, preferably wherein the catalytic metal comprises molybdenum.

Aspect 8: The process of any one or more of the preceding aspects, wherein the inorganic support comprises at least one zeolite selected from zeolite Y, zeolite X, mordenite, ZSM-5, ALPO-5, VPI-5, FSM-16, MCM-22, or MCM-41, preferably comprises at least one zeolite selected from MCM-22 or ZSM-5, more preferably comprises HZSM-5.

Aspect 9: The process of any one or more of the preceding claims, preferably wherein a ratio of silica to alumina in the zeolite is in a range of 10:1 to 50:1, or 13:1 to 30:1, preferably 25:1 to 30:1.

Aspect 10: The process of any one or more of the preceding aspects, further comprising, before the step of contacting, calcining the aromatization catalyst at a calcining temperature in a range of 500° C. to 600° C. and cooling the aromatization catalyst to a temperature less than the calcining temperature.

Aspect 11: A calcined aromatization catalyst activated by the process of any one or more of the preceding aspects.

Aspect 12: A process for aromatization of methane, the method comprising: reacting the methane in the presence of the calcined aromatization catalyst of Aspect 11 to obtain at least one of benzene, naphthalene, toluene, xylene, ethylbenzene, or methyl-naphthalene.

Aspect 13: The process of Aspect 12, further comprising feeding at least one of carbon dioxide or carbon monoxide to the aromatization reactor, preferably feeding a total amount of carbon dioxide and carbon monoxide to the aromatization reactor in a range of 0.6 volume % to 1 volume %, based on the total volume of the methane, the carbon dioxide, and the carbon monoxide.

Aspect 14: The process of Aspect 12 or Aspect 13, wherein the methane is reacted at a temperature in a range of 700° C. to 850° C., 700° C. to 825° C., preferably 700° C. to 800° C.

Aspect 15: The process of any one or more of Aspects 12-14, wherein the methane is reacted at a pressure of greater than 400 kPa, or in a range of 400 kPa to 800 kPa, or 450 kPa to 750 kPa, or 500 kPa to 700 kPa, or 500 kPa to 600 kPa.

Aspect 16: The process of any one or more of Aspects 12-15, wherein the methane is fed to the aromatization reactor at a gas hourly space velocity in a range of 1,000 ml·$g^{-1}$ $hr^{-1}$ to 30,000 ml·$g^{-1}$ $hr^{-1}$, or 2,000 ml $g^{-1}$ $hr^{-1}$ to 29,000 ml·$g^{-1}$ $hr^{-1}$, preferably 3,000 ml·$g^{-1}$ $hr^{-1}$ to 28,000 ml·$g^{-1}$ $hr^{-1}$.

Aspect 17: The process of any one or more of Aspects 12-16, wherein a benzene productivity is equal to or greater than 300 g benzene/kgCat./hr, equal to or greater than 400 g benzene/kgCat./hr, or 500 g benzene/kgCat./hr to 800 g benzene/kgCat./hr, preferably 600 g benzene/kgCat./hr to 700 g benzene/kgCat./hr.

Aspect 18: The use of the aromatization catalyst of Aspect 11 to produce at least one of benzene, naphthalene, toluene, xylene, ethylbenzene, or methyl-naphthalene.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or" unless clearly indicated otherwise by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The terms "optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A process for activating an aromatization catalyst, the process comprising:
    contacting the aromatization catalyst with a carburizing gas in a carburization reactor at a carburization pressure in a range of 500 kPa to 700 kPa to obtain a calcined aromatization catalyst; and
    maintaining the carburization reactor at the carburization pressure for a time of 240 minutes to 480 minutes, and wherein the carburizing gas provides a carbon source.

2. The process of claim 1, further comprising increasing a temperature in the carburization reactor from room temperature to a temperature in a range of 400° C. to 700° C. during contacting of the aromatization catalyst with the carburizing gas.

3. The process of claim 2, wherein increasing the temperature in the carburization reactor comprises increasing the temperature at a rate in a range of 2° C. to 10° C. per minute.

4. The process of claim 1, wherein the carburizing gas comprises hydrogen, methane, ethane, propane, butane, or carbon monoxide, and wherein a volume ratio of methane to hydrogen is in a range of 5:95 to 30:70.

5. The process of claim 1, wherein the aromatization catalyst comprises a catalytic metal on an inorganic support.

6. The process of claim 1, wherein the inorganic support comprises at least one zeolite selected from zeolite Y, zeolite X, mordenite, ZSM-5, ALPO-5, VPI-5, FSM-16, MCM-22, or MCM-41.

7. The process of claim 6, wherein a ratio of silica to alumina in the zeolite is in a range of 10:1 to 50:1.

8. The process of claim 1, further comprising, before the step of contacting, calcining the aromatization catalyst at a calcining temperature in a range of 500° C. to 600° C. and cooling the aromatization catalyst to a temperature less than the calcining temperature.

9. The process of claim 1,
    wherein:
    the process further comprises
        before the step of contacting, calcining the aromatization catalyst at a calcining temperature in a range of 500° C. to 600° C. and cooling the aromatization catalyst to a temperature less than the calcining temperature, and
        increasing a temperature in the carburization reactor from room temperature to a temperature in a range of 400° C. to 700° C. at a rate in a range of 2° C. to 10° C. per minute during contacting of the aromatization catalyst with the carburizing gas;
    the carburization pressure is in a range of greater than 500 kPa to 600 kPa;
    the carburizing gas is fed to the carburization reactor at a gas hourly space velocity in a range of 7,000 ml·g$^{-1}$ hr$^{-1}$ to 10,000 ml·g$^{-1}$ hr$^{-1}$;
    the carburizing gas comprises methane and hydrogen, and a volume ratio of methane to hydrogen is in a range of 15:85 to 20:80;
    the aromatization catalyst comprises molybdenum on an inorganic support;
    the inorganic support comprises HZSM-5; and
    a ratio of silica to alumina in the HZSM-5 is in a range of 25:1 to 30:1.

10. A calcined aromatization catalyst activated by the process of claim 9.

11. A process for aromatization of methane, the method comprising:

reacting the methane in the presence of the calcined aromatization catalyst of claim 9 to obtain at least one of benzene, naphthalene, toluene, xylene, ethylbenzene, or methyl-naphthalene; and feeding at least one of carbon dioxide or carbon monoxide to the aromatization reactor in a total amount in a range of 0.6 volume % to 1 volume %, based on a total volume of the methane, the carbon dioxide, and the carbon monoxide;

wherein the methane is reacted at a temperature in a range of 700° C. to 800° C. and a pressure of 500 kPa to 600 kPa, the methane is fed to the aromatization reactor at a gas hourly space velocity in a range of 3,000 ml·g$^{-1}$ hr$^{-1}$ to 28,000 ml·g$^{-1}$ hr$^{-1}$, and a benzene productivity is 600 g benzene/kgCat./hr to 700 g benzene/kgCat./hr.

12. A calcined aromatization catalyst activated by the process of claim 1.

13. A process for aromatization of methane, the method comprising:

reacting the methane in the presence of the calcined aromatization catalyst of claim 12 to obtain at least one of benzene, naphthalene, toluene, xylene, ethylbenzene, or methyl-naphthalene.

14. The process of claim 13, further comprising feeding carbon dioxide to an aromatization reactor in which the methane is reacted in the presence of the calcined aromatization catalyst, wherein a total amount of carbon dioxide and carbon monoxide fed to the aromatization reactor is in a range of 0.6 volume % to 1 volume %, based on the total volume of the methane, the carbon dioxide, and the carbon monoxide.

15. The process of claim 13, wherein the methane is reacted at a temperature in a range of 700° C. to 850° C.

16. The process of claim 13, wherein the methane is reacted at a pressure of greater than 400 kPa.

17. The process of claim 13, wherein the methane is fed to the aromatization reactor at a gas hourly space velocity in a range of 1,000 ml·g$^{-1}$ hr$^{-1}$ to 30,000 ml·g$^{-1}$ hr$^{-1}$.

18. The process of claim 13, wherein a benzene productivity is equal to or greater than 300 g benzene/kgCat./hr.

19. A process for activating an aromatization catalyst, the process comprising:

contacting the aromatization catalyst with a carburizing gas in a carburization reactor at a carburization pressure in a range of 500 kPa to 700 kPa to obtain a calcined aromatization catalyst, wherein the carburizing gas is fed to the carburization reactor at a gas hourly space velocity in a range of 7,000 ml·g$^{-1}$ hr$^{-1}$ to 10,000 ml·g$^{-1}$ hr$^{-1}$, and wherein the carburizing gas provides a carbon source.

20. A process for activating an aromatization catalyst, the process comprising:

contacting the aromatization catalyst with a carburizing gas in a carburization reactor at a carburization pressure in a range of greater than 300 kPa to 800 kPa to obtain a calcined aromatization catalyst; and maintaining the carburization reactor at the carburization pressure for a time of 240 minutes to 480 minutes, wherein the carburizing gas is fed to the carburization reactor at a gas hourly space velocity in a range of 7,000 ml·g$^{-1}$ hr$^{-1}$ to 10,000 ml·g$^{-1}$ hr$^{-1}$, and wherein the carburizing gas provides a carbon source.

\* \* \* \* \*